(12) United States Patent
Fukuma et al.

(10) Patent No.: US 10,456,034 B2
(45) Date of Patent: Oct. 29, 2019

(54) OPHTHALMIC MICROSCOPE SYSTEM (71) Applicant: KABUSHIKI KAISHA TOPCON, Itabashi-ku (JP)

(72) Inventors: Yasufumi Fukuma, Wako (JP); Kazuhiro Oomori, Setagaya-ku (JP); Satoshi Yamamoto, Saitama (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 190 days.

(21) Appl. No.: 15/049,292

(22) Filed: Feb. 22, 2016

(65) Prior Publication Data
US 2016/0278635 A1 Sep. 29, 2016

(30) Foreign Application Priority Data
Mar. 27, 2015 (JP) ................. 2015-065697

(51) Int. Cl.
*A61B 3/13* (2006.01)
*A61B 3/00* (2006.01)
(Continued)

(52) U.S. Cl.
CPC ............ *A61B 3/132* (2013.01); *A61B 3/0025* (2013.01); *A61B 3/102* (2013.01); *A61F 9/008* (2013.01);
(Continued)

(58) Field of Classification Search
CPC ....... A61B 3/0025; A61B 3/102; A61B 3/132; A61F 9/008; A61F 9/00821; A61F 2009/00851
See application file for complete search history.

(56) References Cited

U.S. PATENT DOCUMENTS 4,443,075 A * 4/1984 Crane ..................... A61F 9/008
606/18
4,601,550 A * 7/1986 Yoshino ................. G02B 21/22
359/834

(Continued)

FOREIGN PATENT DOCUMENTS

JP S60-035707 A 2/1985
JP 2004-503278 A 2/2004
(Continued)

OTHER PUBLICATIONS

Office Action dated Nov. 27, 2018 in Japanese Patent Application No. 2015-065697 w/translation.

*Primary Examiner* — Christopher Koharski
*Assistant Examiner* — Natasha Patel
(74) *Attorney, Agent, or Firm* — Oblon, McClelland, Maier & Neustadt, L.L.P.

(57) ABSTRACT

According to one embodiment, an ophthalmic microscope system includes an illumination system, a pair of light-receiving systems, and an irradiation system. The illumination system is configured to irradiate a subject's eye with illumination light. Each of the light-receiving systems includes a first objective lens and a first imaging device, and is configured to guide the illumination light returning from the subject's eye to the first imaging device through the first objective lens. The objective optical axes of the light-receiving systems are not parallel to each other. The irradiation system is configured to irradiate the subject's eye with light different from the illumination light from a direction different from the objective optical axes.

18 Claims, 6 Drawing Sheets

(51) Int. Cl.
*A61B 3/10* (2006.01)
*A61F 9/008* (2006.01)
(52) U.S. Cl.
CPC .................... *A61F 9/00821* (2013.01); *A61F 2009/00851* (2013.01)

(56) References Cited

U.S. PATENT DOCUMENTS

| | | |
|---|---|---|
| 7,599,591 B2 | 10/2009 | Andersen et al. |
| 8,123,353 B2 * | 2/2012 | Biernat .................. A61F 9/008 351/205 |
| 8,922,882 B2 | 12/2014 | Hauger et al. |
| 2012/0184857 A1 * | 7/2012 | Yokosuka ........... A61F 9/00821 600/476 |
| 2016/0038025 A1 * | 2/2016 | Irsch ........................ A61B 3/10 351/215 |
| 2017/0042419 A1 * | 2/2017 | Nakanishi ............... A61F 9/007 |

FOREIGN PATENT DOCUMENTS

| | | |
|---|---|---|
| JP | 2005-049646 A | 2/2005 |
| JP | 2008-088435 A | 4/2008 |
| JP | 2011-512918 A | 4/2011 |

* cited by examiner

OPHTHALMIC MICROSCOPE SYSTEM

CROSS-REFERENCE TO RELATED APPLICATION

This application is based upon and claims the benefit of priority from Japanese Patent Application No. 2015-065697, filed 27 Mar. 2015; the entire contents of which are incorporated herein by reference.

FIELD

Embodiments described herein relate generally to an ophthalmic microscope system.

BACKGROUND

Various types of microscopes are used in the ophthalmic field to observe an enlarged view of the eye. Examples of the ophthalmic microscopes include slit lamp microscopes, surgical microscopes, and the like. Some ophthalmic microscopes include an imaging device to capture images of the eye and a binocular optical system to provide binocular disparity for stereoscopic vision.

The ophthalmic microscope is sometimes used in combination with another ophthalmic device. For example, there are known systems formed of a combination of the ophthalmic microscope and an optical coherence tomography (OCT) device or a laser treatment device (see, for example, U.S. Pat. Nos. 7,599,591 and 8,922,882). The OCT device is used to acquire cross-sectional images and three-dimensional images of the eye, measure the size of a tissue of the eye (retinal thickness, etc.), acquire information on the function of the eye (blood flow information, etc.), and the like. The laser treatment device is used for photocoagulation treatment of the retina or the corner, and the like.

The conventional ophthalmic microscope systems include a Galilean stereomicroscope. The Galilean stereomicroscope is characterized in that the binocular optical system is provided with a common objective lens and that the left and right optical axes of the binocular optical system are parallel to each other. The Galilean stereomicroscope has the benefit of being easily combined with another optical system or an optical element.

Meanwhile, the Galilean stereomicroscope needs an objective lens having a large diameter, and therefore, the degree of freedom in optical design and mechanical design is restricted.

In addition, there is a limit on the distance between the left and right eyes (eye width) of the viewer. Therefore, it is difficult to increase the stereo angle of the binocular optical system, resulting in difficulty of acquiring an observation image having a three-dimensional appearance. In particular, it is extremely difficult to obtain an observation image having a three-dimensional appearance in the observation at a high magnification. On the other hand, it is possible to reduce the stereo angle. However, this requires to place a dedicated optical element (e.g., prism, etc.) in the binocular optical system, which leads to the complication of the structure of the optics. Further, it is also difficult to finely adjust the stereo angle.

A problem exists also in the operability. For example, complicated operation is required for adjusting the focus position according to the observation site. Typically, to shift from the anterior segment observation to the fundus observation, it is necessary to move the microscope in the longitudinal (front-back) direction.

As described above, there are problems in the conventional ophthalmic microscope systems.

SUMMARY

Embodiments are intended to provide a novel structure for the ophthalmic microscope system to solve at least one of the above problems.

According to one embodiment, an ophthalmic microscope system includes an illumination system, a pair of light-receiving systems, and an irradiation system. The illumination system is configured to irradiate a subject's eye with illumination light. Each of the light-receiving systems includes a first objective lens and a first imaging device, and is configured to guide the illumination light returning from the subject's eye to the first imaging device through the first objective lens. The objective optical axes of the light-receiving systems are not parallel to each other. The irradiation system is configured to irradiate the subject's eye with light different from the illumination light from a direction different from the objective optical axes.

DETAILED DESCRIPTION

Referring now to the drawings, a description is given of an ophthalmic microscope system according to embodiments. The disclosure of the references cited in this specification may be incorporated herein by reference.

The ophthalmic microscope system is used for treatment and surgery in the ophthalmic field to observe (photograph) an enlarged image of the subject's eye. Any portion of the subject's eye may be an object to be observed. Examples of the observation object include the cornea, the corner, the vitreous body, the crystalline lens, and the ciliary body in the anterior segment of the eye, and the retina, the choroid, and the vitreous body in the posterior segment. The observation object may also be a peripheral portion of the eye, such as the eyelid and the eye socket.

As well as functioning as a microscope for observing an enlarged view of the eye, the ophthalmic microscope system has the function of another ophthalmic device. Examples of the function as another ophthalmic device include OCT, laser treatment, ocular axial length measurement, refractive power measurement, higher-order aberration measurement, and the like. The other ophthalmic device has an arbitrary configuration capable of examining, measuring or imaging the subject's eye by using an optical technique. In the following embodiment, an example is described in which OCT function and laser treatment function are combined with a microscope.

<Configuration>

Figure 1:
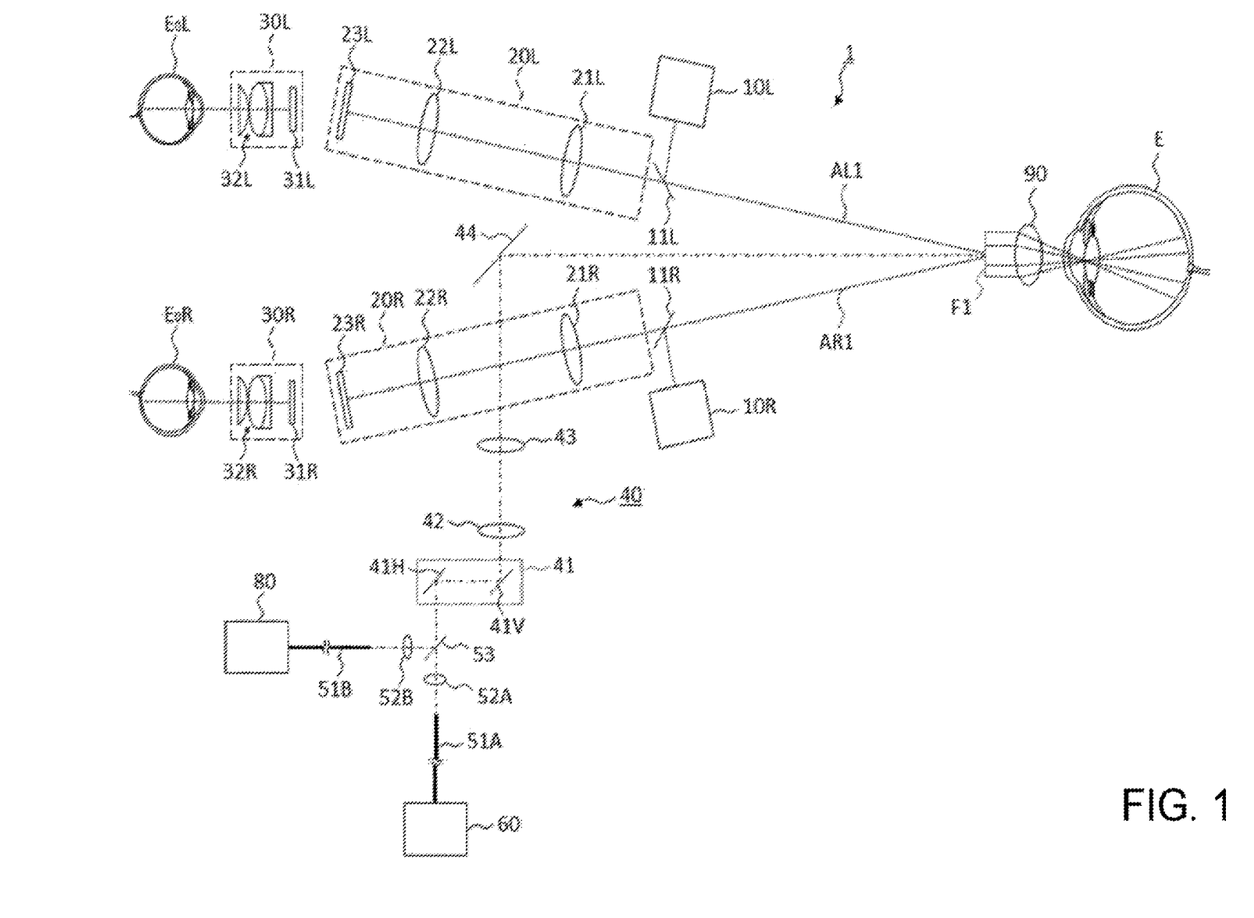
FIG. 1 is a schematic diagram illustrating an example of the configuration of an ophthalmic microscope system according to an embodiment.
Figure 2:
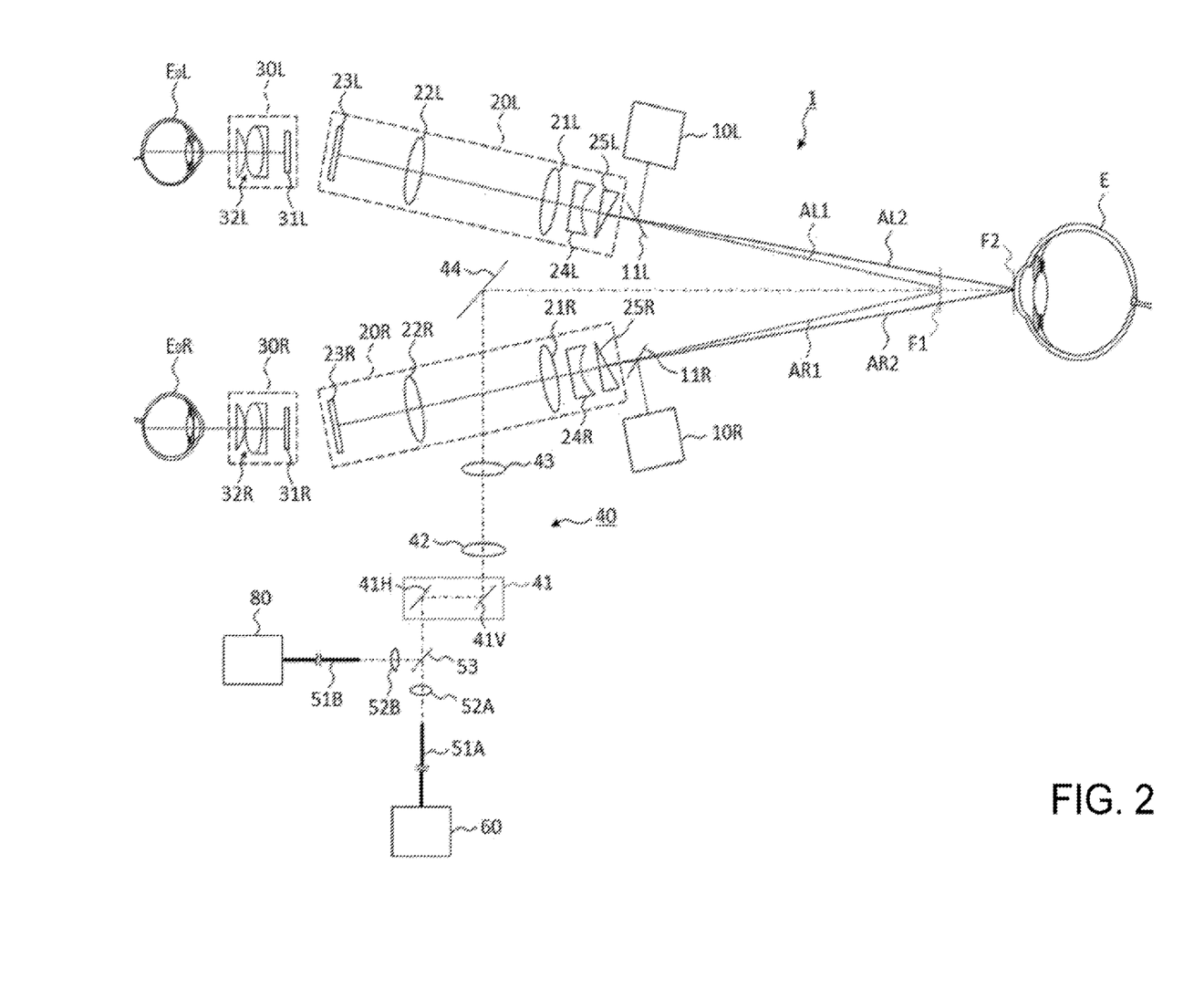
FIG. 2 is a schematic diagram illustrating an example of the configuration of the ophthalmic microscope system of the embodiment.
Figure 3:
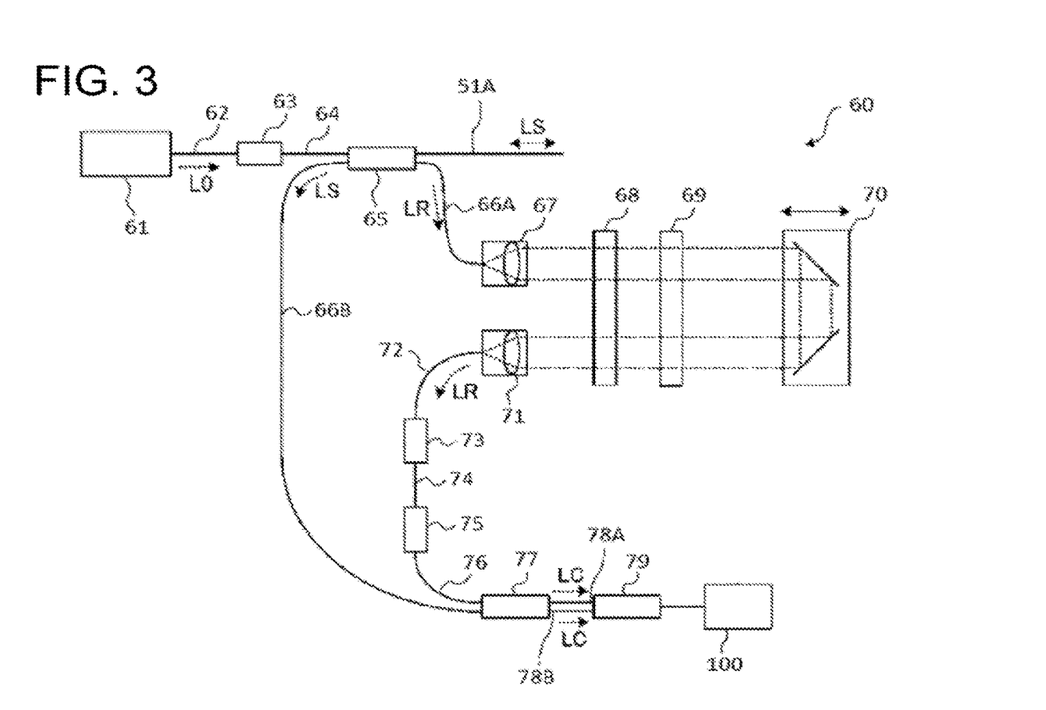
FIG. 3 is a schematic diagram illustrating an example of the configuration of the ophthalmic microscope system of the embodiment.
Figure 4:
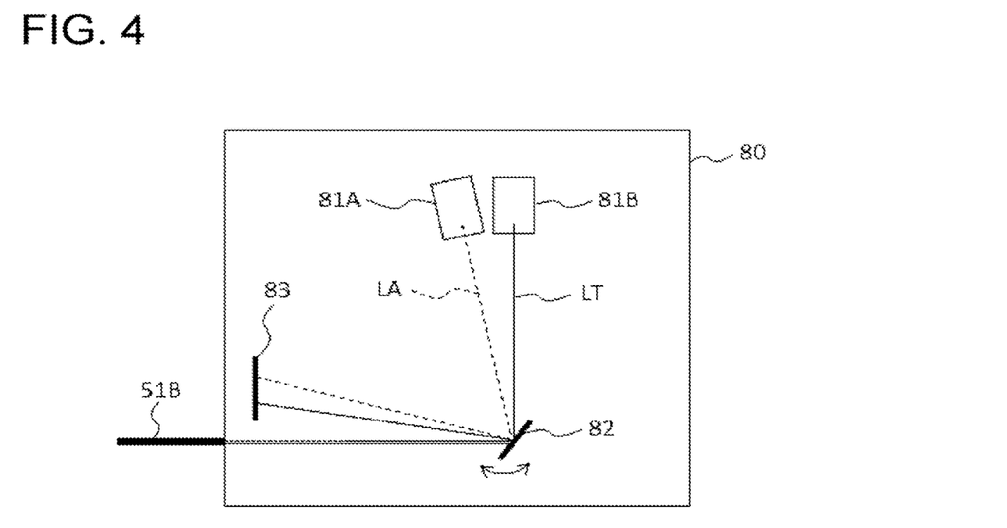
FIG. 4 is a schematic diagram illustrating an example of the configuration of the ophthalmic microscope system of the embodiment.
Figure 5:
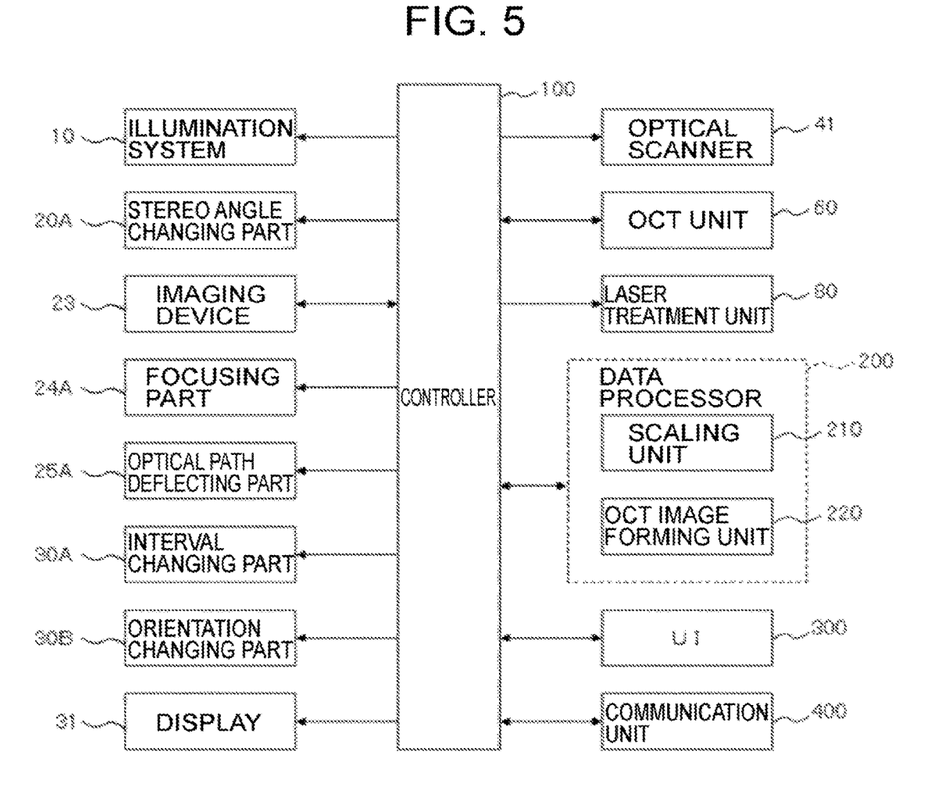
FIG. 5 is a schematic diagram illustrating an example of the configuration of the ophthalmic microscope system of the embodiment.

FIGS. 1 to 5 illustrate the configuration of an ophthalmic microscope system 1 according to an embodiment. FIGS. 1 to 4 illustrate the configuration of the optical system. FIG. 1 illustrates the optical system when the posterior segment of the eye is being observed. FIG. 2 illustrates the optical system when the anterior segment is being observed. FIGS. 3 and 4 illustrate the optical system providing the function as another ophthalmic device described above. FIG. 5 illustrates the configuration of the processing system.

The ophthalmic microscope system 1 includes illumination systems 10 (10L, 10R), light-receiving systems 20 (20L, 20R), ocular systems 30 (30L, 30R), an irradiation system 40, an OCT unit 60, and a laser treatment unit 80. During the observation of the posterior segment of the eye (the retina, etc.), a front lens 90 is placed immediately before the subject's eye E. Incidentally, instead of the non-contact front lens 90 as illustrated in FIG. 1, a contact lens or the like can be used. Besides, a contact mirror (triple mirror, etc.) or the like can be used for observing the corner.

(Illumination Systems 10)

The illumination systems 10 illuminate the subject's eyes E with illumination light. Although not illustrated, the illumination systems 10 each include a light source that emits illumination light, an aperture that defines the illumination field, a lens system, and the like. The illumination systems 10 may have the same configuration as that of conventional ophthalmic devices (e.g., slit lamp microscope, fundus camera, refractometer, etc.).

The illumination systems 10L and 10R of the embodiment are configured to be coaxial with the light-receiving systems 20L and 20R, respectively. Specifically, a beam splitter 11L formed of, for example, a half mirror is obliquely arranged with respect to the left light-receiving system 20L for obtaining an image to be presented to the viewer's left eye $E_OL$. The beam splitter 11L couples the optical path of the left illumination system 10L with the optical path of the left light-receiving system 20L. The illumination light output from the left illumination system 10L is reflected by the beam splitter 11L, and illuminates the subject's eye E in coaxial with the left light-receiving system 20L. Similarly, a beam splitter 11R for coupling the optical path of the right illumination system 10R with the optical path of the right light-receiving system 20R is obliquely arranged with respect to the right light-receiving system 20R for obtaining an image to be presented to the viewer's right eye $E_OR$.

The position of the illumination light can be varied with respect to the optical axis of the light-receiving system 20L (20R). A configuration for this can be implemented by, for example, providing a means for changing the irradiation position of the illumination light to the beam splitter 11L (11R), as in a conventional ophthalmic surgical microscope.

Although, in this example, the beam splitter 11L (11R) is located between the subject's eye E and an objective lens 21L (21R), the optical path of illumination light may be coupled with the light-receiving system 20L (20R) at any position in the light-receiving system 20L (20R).

(Light-Receiving Systems 20)

In this embodiment, there is provided a pair of the left and right light-receiving systems 20L and 20R. The left light-receiving system 20L is configured to obtain an image to be presented to the viewer's left eye $E_OL$. The right light-receiving system 20R is configured to obtain an image to be presented to the right eye $E_OR$. The left light-receiving system 20L and the right light-receiving system 20R have the same configuration. The left light-receiving system 20L (the right light-receiving system 20R) includes the objective lens 21L (21R), an imaging lens 22L (22R), and an imaging device 23L (23R).

The imaging lens 22L (22R) may be dispensed with. When the imaging lens 22L (22R) is provided as in this embodiment, a path between the objective lens 21L (21R) and the imaging lens 22L (22R) may be configured as an afocal optical path (parallel optical path). Thus, it is facilitated to arrange an optical element such as a filter, and to couple with an optical path from another optical system by an optical path coupling member (i.e., the flexibility and extensibility of the optical structure are improved).

Sign AL1 indicates the optical axis (objective optical axis) of the objective lens 21L of the left light-receiving system 20L. Sign AR1 indicates the optical axis (objective optical axis) of the objective lens 21R of the right light-receiving system 20R. The imaging device 23L (23R) may be an area sensor such as a charge-coupled device (CCD) image sensor, a complementary metal-oxide semiconductor (CMOS) image sensor, or the like.

Described above is the configuration of the light-receiving systems 20 for observing the posterior segment (fundus) of the subject's eye (FIG. 1). On the other hand, to observe the anterior eye segment, as illustrated in FIG. 2, a focus lens 24L (24R) and a wedge prism 25L (25R) are each arranged in a position on the subject's eye E side with respect to the objective lens 21L (21R). The focus lens 24L (24R) of this example is a concave lens, and acts to increase the focal length of the objective lens 21L (21R). The wedge prism 25L (25R) deflects the optical path (objective optical axis AL1 (AR1)) of the left light-receiving system 20L (the right light-receiving system 20R) to the outside by a predetermined angle (indicated by signs AL2 and AR2). In this manner, the focus lens 24L and the wedge prism 25L are placed in the left light-receiving system 20L. Similarly, the focus lens 24R and the wedge prism 25R are placed in the right light-receiving system 20R. Thereby, a focus position F1 for posterior eye segment observation can be switched to a focus position F2 for anterior eye segment observation.

A convex lens can be used as the focus lens. In this case, the focus lens is placed in the optical path at the time of the observation of the posterior segment of the subject's eye, and is retracted from the optical path at the time of the observation of the anterior segment. Instead of the insertion/retraction of the focusing lens to change the focal length, for example, a focus lens that is movable in the optical axis direction may be provided to continuously or stepwisely change the focal length.

In the example of FIG. 2, while the direction of the base of the wedge prism 25L (25R) is the outside (i.e., base-out arrangement), a wedge prism for base-in arrangement may be used. In this case, the wedge prism is placed on the optical path at the time of the observation of the posterior segment of the subject's eye, and is retracted from the optical path at the time of the observation of the anterior segment. Instead of the insertion/retraction of the wedge prisms to change the direction of the optical path, a prism having a variable prism amount (and a variable prism direction) may be provided to continuously or stepwisely change the direction of the optical path.

(Ocular Systems 30)

In this embodiment, there is provided a pair of the left and right ocular systems 30L and 30R. The left ocular system 30L is configured to present an image of the subject's eye E obtained by the left light-receiving system 20L to the viewer's left eye $E_oL$. The right ocular system 30L is configured to present an image of the subject's eye E obtained by the right light-receiving system 20L to the right eye $E_oR$. The left ocular system 30L and the right ocular system 30R have the same configuration. The left ocular system 30L (the right ocular system 30R) includes a display 31L (31R), and an ocular lens system 32L (32R).

The display 31L (31R) is a flat panel display such as a liquid crystal display (LCD), or the like. The display 31L (31R) has a display surface in a size (diagonal length) of, for example, 7 inches or less. The screen size of the display devices provided in the left and right ocular systems 30L and 30R is restricted by the eye width of the viewer (pupillary distance, etc.), the size of the apparatus, the design of the apparatus (the arrangement of the optical systems and mechanisms), and the like. That is, such restriction conditions and the extent of the field of view are in a trade-off relationship. From this point of view, the maximum screen size of the displays 31L and 31R is presumably about 7 inches. Incidentally, by devising the configuration of the ocular lens systems 32L and 32R and the arrangement of mechanisms, the displays 31L and 31R having a screen larger than 7 inches or a smaller screen can be used.

As described below, the distance between the left ocular system 30L and the right ocular system 30R can be changed. Accordingly, it is possible to adjust the distance between the left ocular system 30L and the right ocular system 30R according to the eye width of the viewer. Besides, the relative orientation of the left ocular system 30L and the right ocular system 30R can also be changed. In other words, it is possible to change the angle between the optical axes of the left and right ocular systems 30L and 30R. With this, it is possible to induce binocular convergence of the eyes $E_oL$ and $E_oR$, thereby supporting the stereoscopic view of the viewer.

(Irradiation System 40)

The irradiation system 40 irradiates the subject's eye E with light for realizing the function of "another ophthalmic device" described above from a direction different than the objective optical axes (AL1 and AR1, and, AL2 and AR2) of the light-receiving systems 20. The irradiation system 40 of this embodiment irradiates the subject's eye E with light for OCT (measurement light) and light for laser treatment (aiming light, treatment laser beam).

The irradiation system 40 includes an optical scanner 41, an imaging lens 42, a relay lens 43, and a deflecting mirror 44. The light from the OCT unit 60 and the laser treatment unit 80 is guided to the optical scanner 41.

The light (measurement light) from the OCT unit 60 is guided through an optical fiber 51A, and is emitted from the fiber end face. A collimator lens 52A is located in a position facing the fiber end face. The measurement light collimated by the collimator lens 52A into a parallel light flux is directed to an optical path coupling member 53 that couples the optical path for OCT with the optical path for laser treatment. On the other hand, the light from the laser treatment unit 80 (aiming light, treatment laser beam) is guided through an optical fiber 51B, and is emitted from the fiber end face. A collimator lens 52B is located in a position facing the fiber end face. The measurement light collimated by the collimator lens 52B into a parallel light flux is guided to the optical path coupling member 53.

If the wavelength for OCT is different from the wavelength for laser treatment, a dichroic mirror can be used as the optical path coupling member 53. Typically, broadband light with a center wavelength of approximately 1050 nm can be used as the light for OCT. Besides, a laser beam with a wavelength of about 635 nm can be used as the light for laser treatment (as the aiming light, any visible light can be used, for example). On the other hand, if both the wavelengths are substantially the same or close to each other, a half mirror can be used as the optical path coupling member 53. For another example, if the timing of performing OCT is different from the timing of performing laser treatment, an optical path switching member such as a quick return mirror can be used as the optical path coupling member 53. In the example illustrated in FIG. 1 or the like, the measurement light from the OCT unit 60 passes through the optical path coupling member 53 and enters the optical scanner 41. The light from the laser treatment unit 80 is reflected by the optical path coupling member 53 and enters the optical scanner 41.

The optical scanner 41 is a two-dimensional optical scanner, and includes an x scanner 41H configured to deflect the light in the horizontal direction (x direction), and a y scanner 41V configured to deflect the light in the vertical direction (y direction). The x scanner 41H and the y scanner 41V may each be an optical scanner of any form, and, for example, galvanometer mirrors are used. The optical scanner 41 is located in, for example, the position of the exit pupil of each of the collimator lenses 52A and 52B or the vicinity thereof. In addition, the optical scanner 41 is located in, for example, the position of the entrance pupil of the imaging lens 42 or the vicinity thereof.

When two one-dimensional optical scanners are combined into a two-dimensional optical scanner as in this example, the two one-dimensional optical scanners are spaced apart by a predetermined distance (e.g., about 10 mm). Therefore, for example, any of the one-dimensional optical scanners can be placed in the exit pupil position and/or the entrance pupil position.

The imaging lens 42 once forms an image of the parallel light flux (measurement light, aiming light, treatment laser beam) having passed through the optical scanner 41. Further, to form an image of the light again at the subject's eye E (more specifically, at a portion to be observed such as the fundus or the cornea), the light is relayed by the relay lens 43, and is reflected toward the subject's eye E by the deflecting mirror 44.

The position of the deflecting mirror 44 is determined in advance such that the light that has been guided by the irradiation system 40 is incident on the subject's eye E from a direction different than the objective optical axes (AL1 and AR1, and, AL2 and AR2) of the light-receiving systems 20. In this example, the deflecting mirror 44 is located in a position between the left light-receiving system 20L and the right light-receiving system 20R, the objective optical axes of which are not parallel to each other. One of the factors that allow such an arrangement is an improvement in the flexibility of the structure of the optics due to the presence of the relay lens 43. In addition, for example, it is possible to design the distance between a position conjugate to the horizontal optical scanner (the x scanner 41H in this example) and the objective lenses 21L and 21R sufficiently small. Thus, the device can be down-sized.

In general, the scannable range (scannable angle) of the optical scanner 41 is limited. The scannable range can be expanded by using the imaging lens 42 (or an imaging lens system) with a variable focal length. Besides, any configuration to expand the scannable range can be employed.

(OCT Unit 60)

The OCT unit 60 includes an interference optical system to perform OCT. FIG. 4 illustrates an example of the configuration of the OCT unit 60. The optical system illustrated in FIG. 4 is an example of a swept-source OCT system. The OCT unit 60 is configured to split the light from a wavelength tunable (wavelength sweeping) light source into measurement light and reference light, and make return light of the measurement light from the subject's eye E interfere with the reference light having traveled through a reference optical path to produce interference light. Thereby, the OCT unit 60 detects the interference light. The interference optical system obtains a signal representing the spectrum of the interference light as the detection result (detection signal) of the interference light, and sends it to a controller 100.

Similarly to the general swept-source OCT device, a light source unit 61 includes a wavelength tunable (wavelength sweeping) light source capable of varying (sweeping) the wavelength of emission light. The light source unit 61 temporally varies the output wavelength in a range of near infrared wavelengths invisible to the human eye.

Light L0 emitted from the light source unit 61 is guided through an optical fiber 62 to a polarization controller 63, and thereby its polarization state is adjusted. The light L0 is then guided through an optical fiber 64 to a fiber coupler 65, and is split into measurement light LS and reference light LR.

The reference light LR is guided through an optical fiber 66A to a collimator 67 and is collimated into a parallel light flux. The reference light LR then travels through an optical path length correction member 68 and a dispersion compensation member 69, and is guided to a corner cube 70. The optical path length correction member 68 functions as a delay means for matching the optical path length (optical distance) of the reference light LR and the optical path length of the measurement light LS. The dispersion compensation member 69 functions as a dispersion compensation means for matching the dispersion characteristics between the reference light LR and the measurement light LS.

The corner cube 70 turns the traveling direction of the reference light LR in the reverse direction. The corner cube 70 is movable in a direction along the incident and exit optical paths of the reference light LR, and thereby the length of the optical path of the reference light LR is changed. Incidentally, it may be sufficient to provide any one of the means for changing the length of the optical path of the measuring beam LS and the means for changing the length of the optical path of the reference light LR.

The reference light LR that has been reflected by the corner cube 70 travels through the dispersion compensation member 69 and the optical path length correction member 68, and is converted from the parallel light flux into a converging light flux by a collimator 71, and enters an optical fiber 72. The reference light LR is guided to a polarization controller 73, and thereby its polarization state is adjusted. Further, the reference light LR is guided through an optical fiber 74 to an attenuator 75, and the light amount is adjusted under the control of the controller 100. The reference light LR, the amount of which has been adjusted, is then guided through an optical fiber 76 to a fiber coupler 77.

Meanwhile, the measurement light LS generated by the fiber coupler 65 is guided through the optical fiber 51A to be emitted from its end face, and is collimated into a parallel light flux by the collimator lens 52A. The measurement light LS collimated into a parallel light flux travels through a dichroic mirror (the optical path coupling member 53), the optical scanner 41, the imaging lens 42, the relay lens 43, and the deflecting mirror 44, and is incident onto the subject's eye E. The measurement light LS is reflected and scattered at various depth positions of the subject's eye E. The return light of the measurement light LS from the subject's eye E includes reflected light and backscattered light, is guided to the fiber coupler 65 as traveling the same path as the forward path in the reverse direction, and reaches to the fiber coupler 77 via an optical fiber 66B.

The fiber coupler 77 couples the measurement light LS incident via the optical fiber 66B with the reference light LR incident via the optical fiber 76 (by interference) to produce interference light. The fiber coupler 77 divides the interference light at a predetermined branching ratio (e.g., 1:1), and generates a pair of interference light beams LC. The interference light beams LC emitted from the fiber coupler 77 are guided through optical fibers 78A and 78B, respectively, to a detector 79.

The detector 79 may include, for example, a pair of photodetectors for detecting the interference light beams LC, respectively, and a balanced photodiode which outputs a difference in detection results obtained by the photodetectors. The detector 79 sends the detection result (detection signal) to the controller 100.

While swept-source OCT is used in this embodiment, other types of OCT, such as, for example, spectral-domain OCT may also be employed.

(Laser Treatment Unit 80)

The laser treatment unit 80 has a configuration for performing laser treatment. In particular, the laser treatment unit 80 generates light to be projected onto the subject's eye E. The laser treatment unit 80 includes an aiming light source 81A, a treatment light source 81B, a galvanometer mirror 82, and a light-shielding plate 83. Incidentally, the laser treatment unit 80 may include a member other than them. For example, an optical element (lens, etc.), which makes the light generated by the laser treatment unit 80 enter the end face of the optical fiber 51B, may be provided just before the position of the optical fiber 51B.

The aiming light source 81A generates aiming light LA for aiming at a site subjected to laser treatment. Any light source is used as the aiming light source 81A. In this embodiment, aiming operation is carried out while observing an image captured of the subject's eye E. Accordingly, the aiming light source 81A includes a light source (laser light source, light emitting diode, etc.) that emits light of wavelengths at which the imaging device 23 (23L, 23R) has sensitivity. Incidentally, when aiming operation is carried out by visual observation (that is, by observing an optical image, which is not a captured (or photographed) image), visible light is used as the aiming light LA. The aiming light LA is guided to the galvanometer mirror 82.

The treatment light source 81B emits a treatment laser beam (treatment light LT). The treatment light LT may be either a visible laser beam or an invisible laser beam according to the use. In addition, the treatment light source 81B may be a single laser light source or a plurality of laser light sources configured to emit laser light of different wavelengths. The treatment light LT is guided to the galvanometer mirror 82.

The aiming light LA and the treatment light LT are adapted to reach the same position of the reflecting surface of the galvanometer mirror 82. The treatment light LT and the aiming light LA may sometimes be collectively referred to as "irradiation light". The orientation of (the reflecting surface of) the galvanometer mirror 82 is changed to, at least, the orientation to reflect the irradiation light toward the optical fiber 51B (orientation for irradiation) and the orientation to reflect the irradiation light toward the light-shielding plate 83 (orientation for stop).

When the galvanometer mirror 82 is set to the orientation for stop, the irradiation light reaches the light-shielding plate 83. The light-shielding plate 83 is, for example, made of a material and/or in a structure to absorb the irradiation light, and has a light-shielding effect.

In this embodiment, the aiming light source 81A and the treatment light source 81B both emit continuous light. The galvanometer mirror 82 is set to the orientation for irradiation to apply the irradiation light to the subject's eye E. Besides, the galvanometer mirror 82 is set to the orientation for stop to stop applying the irradiation light to the subject's eye E. In another embodiment, the aiming light source 81A and/or the treatment light source 81B may be configured to be capable of generating light intermittently. That is, the aiming light sources 81A and/or the treatment light source 81B may be configured to be able to generate pulse light. The controller 100 performs pulse control for it. In this case, the galvanometer mirror 82 and the light-shielding plate 83 are not needed.

(Controller 100)

The controller 100 controls each part of the ophthalmic microscope system 1 (see FIG. 5). Examples of the control for the illumination systems 10 include turning on and off the light source, light amount adjustment, diaphragm adjustment, and, if slit illumination is available, slit width adjustment. Examples of the control for the imaging device 23 include exposure adjustment, gain adjustment, and imaging rate (capture rate) adjustment.

The controller 100 displays various types of information on the display 31. For example, the controller 100 displays an image captured by the imaging device 23L (or an image obtained by processing the captured image) on the display 31L as well as displaying an image captured by the imaging device 23R (or an image obtained by processing the captured image) on the display 31R.

Examples of the control for the optical scanner 41 may include any of the followings: the controller 100 controls the optical scanner 41 to sequentially deflect the measurement light LS such that the measurement light LS is applied to a plurality of positions corresponding to an OCT scan pattern set in advance; and the controller 100 controls the optical scanner 41 to sequentially deflect the aiming light LA and/or the treatment light LT such that the aiming light LA and/or the treatment light LT are applied to a plurality of positions corresponding to a laser treatment pattern set in advance.

In the OCT unit 60, the controller 100 controls the light source unit 61, the polarization controller 63, the corner cube 70, the polarization controller 73, the attenuator 75, the detector 79, and the like. In the laser treatment unit 80, the controller 100 controls the aiming light source 81A, the treatment light source 81B, the galvanometer mirror 82, and the like.

Further, the controller 100 controls various mechanisms. Examples of the mechanisms include a stereo angle changing part 20A, a focusing part 24A, an optical path deflecting part 25A, an interval changing part 30A, and an orientation changing part 30B.

The stereo angle changing part 20A rotates the left light-receiving system 20L and the right light-receiving system 20R relative to each other. That is, the stereo angle changing part 20A causes relative movement of the left light-receiving system 20L and the right light-receiving system 20R to change the angle formed by their objective optical axes (e.g., AL1 and AR1). By this relative movement, for example, the left light-receiving system 20L and the right light-receiving system 20R are moved by the same angle to the opposite rotation directions. In this movement mode, the direction of the bisector of the angle formed by the objective optical axes (e.g., AL1 and AR1) is fixed. Note that it is also possible to perform the relative movement such that the direction of the bisector is allowed to vary.

The focusing part 24A is configured to insert/retract the left and right focus lenses 24L and 24R into/from the optical path. The focusing part 24A may be configured to simultaneously insert/retract the left and right focus lenses 24L and 24R. For another example, the focusing part 24A may be configured to move the left and right focus lenses 24L and 24R (optionally, at the same time) in the optical axis direction to change the focus position. Alternatively, the focusing part 24A may be configured to change the refractive power of the left and right focus lenses 24L and 24R (optionally, at the same time) to change the focal length.

The optical path deflecting part 25A is configured to insert/retract the left and right wedge prisms 25L and 25R into/from the optical path. The optical path deflecting part 25A may be configured to simultaneously insert/retract the left and right wedge prisms 25L and 25R. For another example, the optical path deflecting part 25A may be configured to change the prism amount (and the prism direction) of the left and right wedge prisms 25L and 25R (optionally, at the same time) to change the orientation of the optical paths of the left and right light-receiving systems 20L and 20R.

The interval changing part 30A changes the distance between the left and right ocular systems 30L and 30R. The interval changing part 30A may be configured to move the left and right ocular systems 30L and 30R relative to each other without changing the relative orientation of their optical axes.

The orientation changing part 30B changes the relative orientation of the left and right ocular systems 30L and 30R. The orientation changing part 30B is configured to move the left and right ocular systems 30L and 30R relative to each other to change the angle formed by their optical axes. By this relative movement, for example, the left ocular system 30L and the right ocular system 30R are moved by the same angle to the opposite rotation directions. In this movement mode, the direction of the bisector of the angle formed by the optical axes is fixed. Note that it is also possible to perform the relative movement such that the direction of the bisector is allowed to vary.

(Data Processor 200)

A data processor 200 performs various types of data processing. The data processing includes image forming, image processing, and the like. The data processor 200 may perform the analysis of an image, an examination result and a measurement result, and may perform processing related to information about the subject (electronic medical record information, etc.). The data processor 200 includes a scaling unit 210 and an OCT image forming unit 220.

The scaling unit 210 expands an image acquired by the imaging device 23. This process is so-called digital zooming, and includes a process of cutting out a part of the image obtained by the imaging device 23, and a process of creating an enlarged image of the part. The area of the image to be cut out is set by the viewer or the controller 100. The scaling unit 210 performs the same process on an image (left image)

acquired by the imaging device 23L of the left light-receiving system 20L, and an image (right image) acquired by the imaging device 23R of the right light-receiving system 20R. Thereby, the images at the same magnification are presented to the left eye $E_0L$ and the right eye $E_0R$ of the viewer.

Incidentally, in addition to or instead of the digital zoom function, so-called optical zoom function may be provided. The optical zoom function is realized by providing a variable magnification lens (variable magnification lens system) to each of the left and right light-receiving systems 20L and 20R. As a specific example, the variable magnification lens may be (selectively) inserted into/retracted from the optical path, or the variable magnification lens may be moved along the optical axis direction. The controller 100 performs control for the optical zoom function.

The OCT image forming unit 220 forms an image of the subject's eye E based on the detection result of the interference light beams LC obtained by the detector 79 of the OCT unit 60. The controller 100 sends detection signals sequentially output from the detector 79 to the OCT image forming unit 220. The OCT image forming unit 220 applies Fourier transform and the like to the spectral distribution based on the detection result obtained by the detector 79, for example, with respect to a series of wavelength scans (for each A-line) to form the reflection intensity profile in each A-line. Further, the OCT image forming unit 220 forms image data by imaging each A-line profile. With this, a B-scan image (sectional image), volume data (three-dimensional image data) and the like can be obtained.

The data processor 200 may have the function of analyzing the image (OCT image) formed by the OCT image forming unit 220. As the analysis function may be cited the function of retinal thickness analysis, comparative analysis with the normal eye, and the like. The analysis function is implemented by using a known application program. Further, the data processor 200 may have the function of analyzing the image acquired by the light-receiving systems 20. The data processor 200 may have the function of analyzing in which analysis of the image acquired by the light-receiving systems 20 and analysis of the OCT image are performed in combination with each other.

(User Interface 300)

A user interface (UI) 300 has a function for exchanging information between the viewer or the like and the ophthalmic microscope system 1. The user interface 300 includes a display device and an operation device (input device). The display device may include the display 31 and/or another display. The operation device includes various hardware keys and/or software keys. At least part of the operation device and at least part of the display device may be integrated with each other. For example, a touch panel display offers the integrated functions of the display device and the operation device.

(Communication Unit 400)

A communication unit 400 is configured to transmit information to another device and receive information sent from another device. The communication unit 400 may include a communications device conforming to a predetermined network (LAN, the Internet, etc.). For example, the communication unit 400 acquires information from an electronic medical record database, a medical image database, or the like via LAN provided in a medical institution. If there is provided an external monitor, the communication unit 400 can transmit images acquired by the ophthalmic microscope system 1 (that is, images obtained by the light-receiving systems 20, OCT images, etc.) substantially in real-time to the external monitor.

<Operations and Effects>

Described below are operations and effects of the embodiment.

According to this embodiment, the ophthalmic microscope system includes illumination systems (10), a pair of light-receiving systems (20L, 20R), and an irradiation system (40). The illumination systems are configured to irradiate a subject's eye with illumination light. Each of the light-receiving systems includes an objective lens (21L, 21R) and an imaging device (23L, 23R). The objective optical axes (AL1, AR1, etc.) of the light-receiving systems are not parallel to each other. Further, the light-receiving systems are each configured to guide return light of the illumination light from the subject's eye to the imaging device through the objective lens. The irradiation system is configured to irradiate the subject's eye with light (the measurement light LS, the aiming light LA, treatment light LT, etc.) different from the illumination light from a direction different from the objective optical axes (AL1, AR1, etc.).

In the ophthalmic microscope system, the light-receiving systems each include an objective lens, and an objective lens having a large diameter, which is common to both the light-receiving systems, is not used. Thus, the flexibility of optical design and mechanical design can be improved, which facilitates the arrangement of the optics (for example, the arrangement of the irradiation system). In addition, the downsizing of the apparatus can be achieved.

The ophthalmic microscope system of this embodiment may include a first mechanism (the stereo angle changing part 20A) configured to change the angle (stereo angle) formed by the objective optical axes of the light-receiving systems. Such a structure can be realized by that the light-receiving systems each have an independent objective lens. In the conventional configuration in which a pair of light-receiving systems shares a common objective lens, the angle (stereo angle) between the light-receiving systems cannot be arbitrarily changed.

With this, a large stereo angle can be realized with a simple structure, and it is possible to obtain an observation image having a three-dimensional appearance. In particular, by applying a sufficiently large stereo angle during an observation at high magnification, an observation image having a three-dimensional appearance can be achieved. Further, fine adjustment of the stereo angle can be facilitated. For example, if the irradiation light, the return light, or the like is blocked by the iris during fundus observation, the stereo angle can be reduced depending on the pupil size of the subject's eye.

Figure 6:
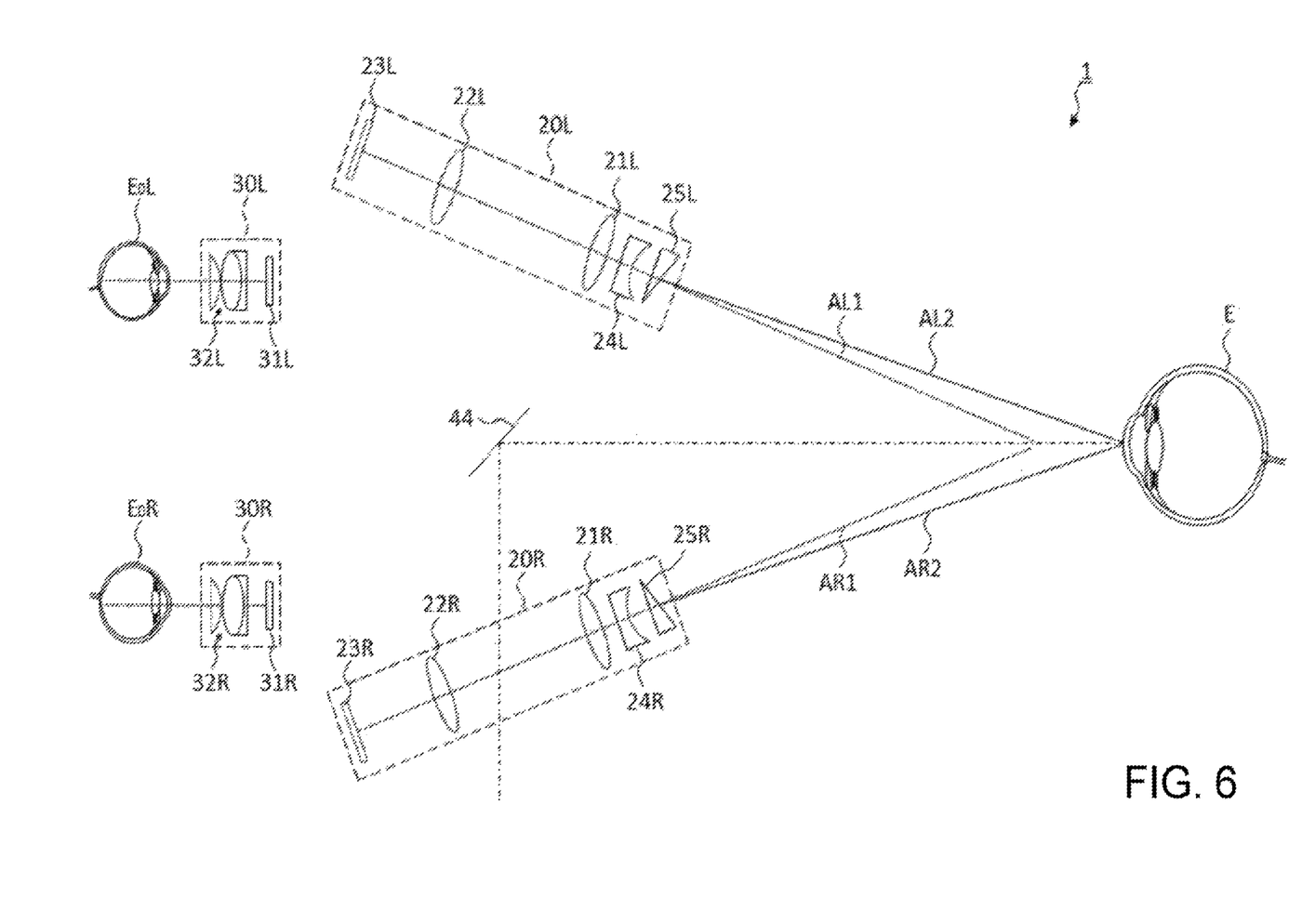
FIG. 6 is a schematic diagram illustrating an action of the ophthalmic microscope system of the embodiment.

FIG. 6 illustrates an example of the optical system in which the stereo angle is increased from the state as illustrated in FIG. 2. Here, the stereo angle may be defined as an angle formed by the objective optical axis AL1 of the left light-receiving system 20L and the objective optical axis AR1 of the right light-receiving system 20R, or an angle formed by the objective optical axis AL2 of the left light-receiving system 20L and the objective optical axis AR2 of the right light-receiving system 20R. If the stereo angle is changed by the stereo angle changing part 20A, the relative position (distance, relative orientation) of the left and right ocular systems 30L and 30R does not change. Besides, according to the change of the stereo angle, control can be performed to prevent a shift in the focus position by adjusting the distance between the left and right light-receiving systems 20L and 20R with respect to the subject's eye E, changing the focal length of the left and right light-receiving systems 20L and 20R, or the like.

In the embodiment, each of the light-receiving systems may include a lens (the focus lens 24L, 24R) for changing the focus position. There may be further provided a second mechanism (the focusing part 24A) configured to move these lenses together. For example, the second mechanism simultaneously inserts the lenses into the respective optical paths, and simultaneously retracts them from the respective optical paths. Alternatively, the second mechanism moves these lenses in parallel.

With this, the focus position can easily be changed depending on the site to be observed. For example, in a conventional structure, it is required to perform an operation to move the microscope itself in the longitudinal direction to shift the site to be observed from the anterior segment to the fundus. On the other hand, according to this embodiment, the focus position can easily be changed by the insertion/retraction of the lenses or the movement of the lenses.

In the embodiment, each of the light-receiving systems may include a deflecting member (the wedge prism 25L, 25R) for deflecting the optical path. There may be further provided a third mechanism (the optical path deflecting part 25A) to move these deflecting members together. For example, the third mechanism simultaneously inserts the deflection members into the respective optical paths, and simultaneously retracts them from the respective optical paths.

With this configuration, the focus position can easily be changed depending on the site to be observed. In particular, by the combination of the configuration with the lenses for changing the focus position and the second mechanism for moving the lenses together, the focus position can be shifted in a more suitable manner.

In the embodiment, there may be provided a third controller (the controller 100) configured to display, on the display, an image based on output from the imaging device of at least one of the light-receiving systems. The display may include a display device provided to the ophthalmic microscope system or a display device provided outside of the ophthalmic microscope system.

With this configuration, an image(s) obtained by the light-receiving systems can be presented. In the case of presenting images obtained by both the light-receiving systems, the images can be displayed so that they provide a stereoscopic image.

As an example in which at least part of the display is provided to the ophthalmic microscope system, there may be provided a pair of ocular units (the ocular systems 30L and 30R). Each of the ocular units include a display (the display 31L, 31R), and one or more lenses (the ocular lens system 32L, 32R) placed on the display surface side of the display.

With this configuration, the viewer can observe a pair of images acquired by the light-receiving systems as if observing optical images through a common binocular eyepiece. By employing such a configuration, it is possible to realize an exit pupil diameter sufficiently large as compared to the conventional microscope, thereby improving visibility and relieving fatigue.

In the embodiment, there may be provided a fourth mechanism (the interval changing part 30A) configured to change the distance between the ocular units.

With this configuration, the distance between the ocular units can be adjusted according to the viewer's eye width (pupillary distance, etc.). Thus, binocular observation can be performed comfortably.

In the embodiment, there may be provided a fifth mechanism (the orientation changing part 30B) configured to change the relative orientation of the ocular units.

With this configuration, a state where the optical axes of the ocular units are arranged in parallel (parallel view) or a state where the optical axes are not parallel to each other (inside view) can be arbitrarily selected by preference, etc. of the viewer. Moreover, by adjusting the angle formed by the optical axes, it is possible to induce binocular convergence of the eyes of the viewer, thereby supporting stereoscopic vision. Further, by combining the convergence adjustment and interpupillary adjustment, the viewer can enjoy stereoscopic vision relatively easily even if he/she has crossed eyes to a certain extent.

In the embodiment, there may be provided a first optical path coupling member (the beam splitter 11L, 11R) configured to respectively couple the optical paths of the illumination systems with the optical paths of the light-receiving systems. In other words, it may be configured that the illumination systems and the light-receiving systems are arranged in a coaxial manner. Incidentally, an example is described later in which the illumination systems and the light-receiving systems are arranged in a non-coaxial manner.

In the embodiment, there may be provided a light-receiving system different from the pair of light-receiving systems (main light-receiving systems). In particular, there may be provided a pair of light-receiving systems different from the main light-receiving systems. As with the main light-receiving systems, the "other light-receiving systems" each may include an objective lens and an imaging device, and their objective optical axes may be arranged in a non-coaxial manner. Further, the other light-receiving systems are each configured to guide the illumination light irradiated to the subject's eye and returning therefrom to the imaging device through the objective lens. The light-receiving systems thus configured are used as, for example, an assistant's microscope. For example, in surgery, the surgeon uses the main light-receiving systems, while assistants use the assistant's microscope. A pair of images acquired by the assistant's microscope is presented, for example, via another pair of ocular systems having the same structure as the (main) ocular systems. In addition, any structure and features regarding the main light-receiving systems and the like can be applied in a similar manner to the assistant's microscope.

In the embodiment, the structure of the illumination systems can be arbitrarily designed. For example, as described in detail above, the irradiation system may include at least one of the function of irradiating the subject's eye with light for OCT (the measurement light LS), and the function of irradiating the subject's eye with light for laser treatment (the aiming light LA, the treatment light LT). Further, the ophthalmic microscope system of this embodiment may include a configuration for OCT (the OCT unit 60, the data processor 200, etc.), and a configuration for laser treatment (the laser treatment unit 80, etc.).

The irradiation system of the above embodiment may include an optical scanner (41) configure to deflect the light applied to the subject's eye. In the above example, although the light for OCT and the light for laser treatment are deflected by a common optical scanner, individual optical scanners can be provided for them.

<Modifications>

The embodiments described above are mere examples for embodying or carrying out the present invention, and therefore susceptible to several modifications and variations (omission, substitution, addition, etc.), all coming within the scope of the invention.

(Modification 1)

In the above embodiment, the focus lenses 24L and 24R as well as the wedge prisms 25L and 25R are retracted from the optical paths at the time of fundus observation, and inserted into the optical paths at the time of anterior eye segment observation. It is possible to automate this operation. In an embodiment, an auxiliary optical member is used to change the site of the subject's eye to be observed. For example, at the time of fundus observation the front lens 90 is placed in the optical path, while at the time of anterior eye segment observation, it is retracted from the optical path.

According to this modification, the ophthalmic microscope system may be configured to change the state of the focus lenses 24L and 24R depending on the state of the auxiliary optical member (i.e., the selection of the site to be observed). For this, in response to a change in the site to be observed by the auxiliary optical member, the controller 100 may control the second mechanism for moving the focus lenses 24L and 24R together. Similarly, in response to a change in the site to be observed by the auxiliary optical member, the controller 100 may control the third mechanism for moving the wedge prisms 25L and 25R together.

Described below are specific examples. When the front lens 90 is retracted from the optical path, the controller 100 controls the focusing part 24A and the optical path deflecting part 25A to insert the focus lenses 24L and 24R as well as the wedge prisms 25L and 25R in the optical path. On the other hand, when the front lens 90 is inserted into the optical path, the controller 100 controls the focusing part 24A and the optical path deflecting part 25A to retract the focus lenses 24L and 24R as well as the wedge prisms 25L and 25R therefrom.

The ophthalmic microscope system of this modification may include a structure for generating information that indicates the state of the auxiliary optical member (e.g., whether or not the front lens 90 is placed in the optical path). For example, the arrangement of an arm that holds the front lens 90 can be detected by using a sensor such as a micro switch. Alternatively, if the insertion/retraction of the front lens 90 is performed based on a signal from the controller 100, the current state of the front lens 90 can be acquired by referring to the history of the control.

For another example, it is possible to determine whether the front lens 90 is located in the optical path based on an image(s) obtained by at least one of the imaging devices 23L and 23R, and on the current states of the focus lenses 24L and 24R as well as the wedge prisms 25L and 25R. For example, the data processor 200 analyzes an image obtained in the state where the focus lens 24L and the like are located in the optical path to determine an amount indicating a blur of the image. If the blur amount is equal to or above a threshold, the front lens 90 is determined to be located in the optical path. On the other hand, when the blur amount is less than the threshold, the front lens 90 is determined to have been retracted from the optical path. In the case of analyzing an image obtained when the focus lens 24L and the like are retracted from the optical path, the state of the front lens 90 can be determined in the same manner.

According to this modification, it is possible to automatically change the state of the lens (the focus lenses 24L and 24R) for changing the focus position, and/or the state of the deflecting member (the wedge prisms 25L and 25R) for deflecting the optical path according to a change in the site to be observed. Therefore, the operability can be further improved.

(Modification 2)

Figure 7:
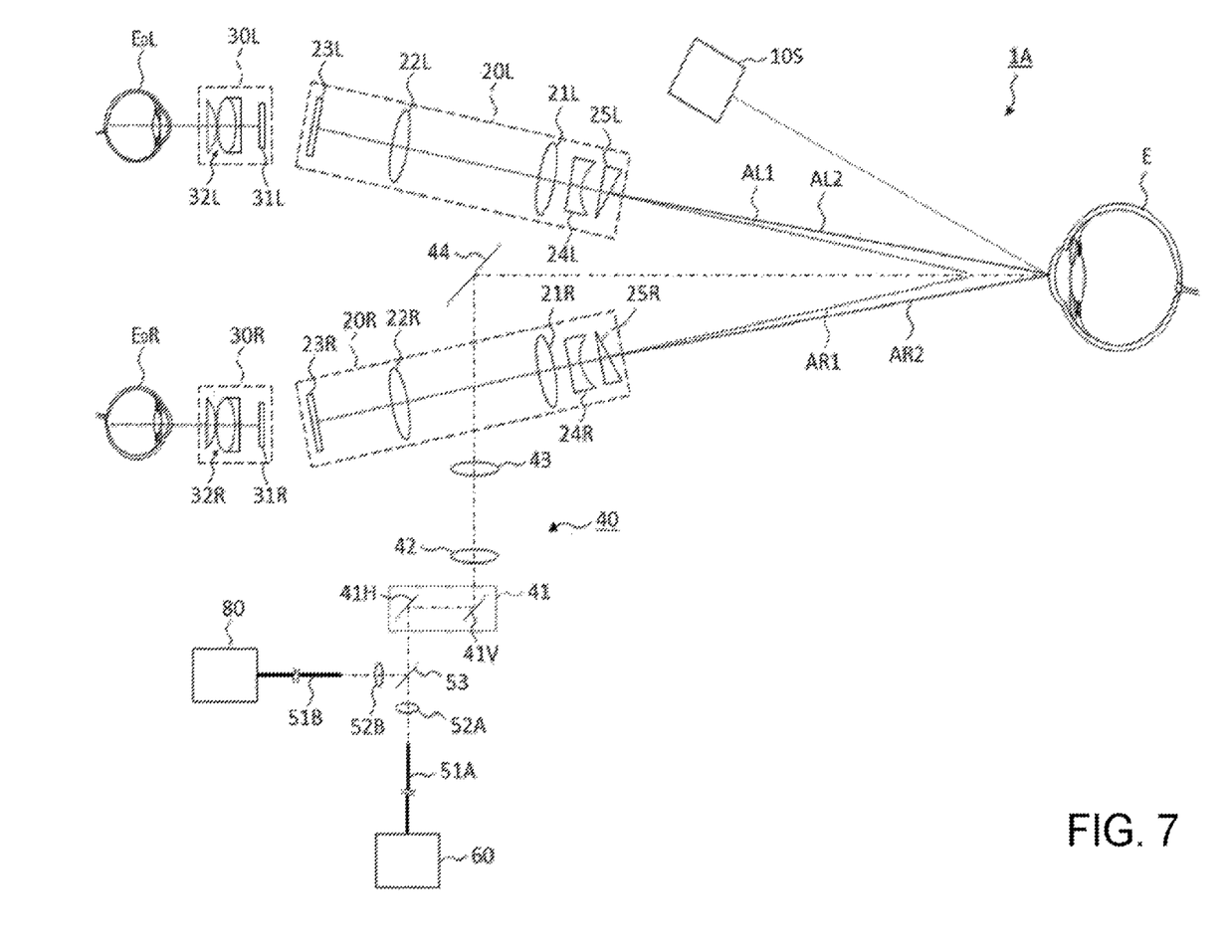
FIG. 7 is a schematic diagram illustrating an example of the configuration of an ophthalmic microscope system according to a modification.

The illumination systems (10L and 10R) of the above embodiment are arranged coaxially with a pair of the light-receiving systems (20L and 20R). In this modification, illumination systems are arranged in a non-coaxial manner with respect to a pair of light-receiving systems. In other words, the illumination systems are configured to project illumination light from a direction different from the objective optical axes of the light-receiving systems. FIG. 7 illustrates an example of the configuration of the optical system of the present modification. An illumination system 10S of an ophthalmic microscope system 1A is, for example, capable of projecting slit light to the subject's eye. As a typical example of the ophthalmic microscope may be cited a slit lamp microscope. In this modification, as in the slit lamp microscope, the relative positions of the illumination system 10S and the light-receiving systems 20L and 20R can be changed. More specifically, the illumination system 10S as well as the light-receiving systems 20L and 20R can be configured to be rotatable about the same axis. Thereby, it is possible for the viewer to observe a cross section of the cornea or the like illuminated by the slit light from an oblique direction.

The ophthalmic microscope system may include either or both of the coaxial illumination systems as described in the above embodiment, and the non-coaxial illumination systems as described in this modification. When provided with both of the illumination systems, for example, the ophthalmic microscope system can switch the illumination systems to be used according to a change in the site to be observed.

While certain embodiments have been described, these embodiments have been presented by way of example only, and are not intended to limit the scope of the inventions. Indeed, the novel embodiments described herein may be embodied in a variety of other forms; Further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmic microscope system, comprising:
    a pair of illumination systems configured to irradiate a subject's eye with illumination light along a pair of illumination optical axis axes;
    a pair of light-receiving systems each including a first objective lens and a first imaging device, configured to guide the illumination light returning from the subject's eye along light returning axes to the first imaging device through the first objective lens, wherein objective optical axes of the light-receiving systems are not parallel to each other, the light returning axes are not parallel to each other, and the illumination optical axes and the light returning axes are not parallel to each other;
    an irradiation system configured to irradiate the subject's eye for treatment with irradiation light different from the illumination light along an irradiation axis that is different from the objective optical axes, the irradiation axis is not parallel to either of the illumination optical axes, and the irradiation axis is not parallel to the light returning axes, wherein the irradiation system comprises a laser treatment unit configured to generate the irradiation light; and
an optical scanner configured to deflect the irradiation light, wherein the ophthalmic microscope system is configured to project the irradiation light deflected by the optical scanner onto the subject's eye, wherein
each of the pair of light-receiving systems includes an optical element arranged between the first objective lens and the subject's eye; and
each of the pair of illumination systems is configured to be coaxial with a corresponding one of the pair of light-receiving systems.

2. The ophthalmic microscope system of claim 1, further comprising a first mechanism configured to change an angle formed by the objective optical axes of the light-receiving systems.

3. The ophthalmic microscope system of claim 1, wherein the light-receiving systems include their respective lenses to change a focus position,
the ophthalmic microscope system further comprising a second mechanism configured to move the lenses together.

4. The ophthalmic microscope system of claim 3, further comprising:
an auxiliary optical member configured to change a site to be observed in the subject's eye; and
a first controller configured to control the second mechanism in response to a change in the site to be observed by the auxiliary optical member.

5. The ophthalmic microscope system of claim 1, wherein the light-receiving systems include their respective deflecting members configured to deflect an optical path,
the ophthalmic microscope system further comprising a third mechanism configured to move the deflecting members together.

6. The ophthalmic microscope system of claim 5, further comprising:
an auxiliary optical member configured to change a site to be observed in the subject's eye; and
a second controller configured to control the third mechanism in response to a change in the site to be observed by the auxiliary optical member.

7. The ophthalmic microscope system of claim 1, further comprising a third controller configured to display, on a display, an image based on output from the first imaging device of at least one of the light-receiving systems.

8. The ophthalmic microscope system of claim 7, further comprising a pair of ocular units each including the display and one or more lenses placed on side of a display surface of the display.

9. The ophthalmic microscope system of claim 8, further comprising a fourth mechanism configured to change a distance between the ocular units.

10. The ophthalmic microscope system of claim 8, further comprising a fifth mechanism configured to change relative orientation of the ocular units.

11. The ophthalmic microscope system of claim 8, wherein size of the display surface of the display is 7 inches or less.

12. The ophthalmic microscope system of claim 1, further comprising a first optical path coupling member configured to couple an optical path of the illumination system with an optical path of each of the light-receiving systems.

13. The ophthalmic microscope system of claim 1, wherein the illumination system is capable of irradiating the subject's eye with the illumination light from a direction different from the objective optical axes of the light-receiving systems.

14. The ophthalmic microscope system of claim 1, further comprising a pair of second light-receiving systems each including a second objective lens and a second imaging device, configured to guide the illumination light returning from the subject's eye to the second imaging device through the second objective lens, wherein objective optical axes of the second light-receiving systems are not parallel to each other.

15. The ophthalmic microscope system of claim 1, further comprising:
an interference optical system configured to split light from an OCT light source into measurement light and reference light, and detect interference light between return light of the measurement light, which has been irradiated to the subject's eye by the irradiation system, and the reference light; and
a data processor configured to generate an image or an analysis result of the subject's eye based on a detection result of the interference light.

16. The ophthalmic microscope system of claim 1, wherein the laser treatment unit comprises a treatment laser light source and an aiming light source, and wherein the irradiation system is configured to irradiate the subject's eye with treatment light output from the treatment laser light source and aiming light output from the aiming light source.

17. The ophthalmic microscope system of claim 1, wherein the laser treatment unit comprises a treatment laser light source and an aiming light source, and wherein the irradiation system is configured to irradiate the subject's eye with treatment light output from the treatment laser light source and aiming light output from the aiming light source,
the ophthalmic microscope system further comprising:
an interference optical system configured to split light from an OCT light source into measurement light and reference light, and detect interference light between return light of the measurement light, which has been irradiated to the subject's eye by the irradiation system, and the reference light;
a data processor configured to generate an image or an analysis result of the subject's eye based on a detection result of the interference light; and
a second optical path coupling member configured to couple an optical path of the irradiation system where the treatment light and the aiming light are guided with an optical path where the measurement light and the return light are guided.

18. An ophthalmic microscope system, comprising:
a pair of illumination systems configured to irradiate a subject's eye with illumination light along illumination optical axes that are not parallel to each other;
a pair of light-receiving systems each including a first objective lens and a first imaging device, configured to guide the illumination light returning from the subject's eye along light returning axes to the first imaging device through the first objective lens, wherein objective optical axes of the light-receiving systems are not parallel to each other, the light returning axes are not parallel to each other, and the illumination optical axes and the light returning axes are not parallel to each other;
an irradiation system configured to irradiate the subject's eye with irradiation light different from the illumination light from a direction different from the objective optical axes, wherein the irradiation system comprises a laser treatment unit configured to generate the irradiation light; and an optical scanner configured to deflect the irradiation light, wherein the ophthalmic microscope system is configured to project the irradiation light deflected by the optical scanner onto the subject's eye, wherein each of the pair of light-receiving systems includes an optical element arranged between the first objective lens and the subject's eye; and each of the pair of illumination systems is configured to be coaxial with a corresponding one of the pair of light-receiving systems.

* * * * *